(12) United States Patent
Harkins, Jr.

(10) Patent No.: US 9,005,183 B2
(45) Date of Patent: Apr. 14, 2015

(54) SYSTEM AND METHOD FOR TREATING ERECTILE DYSFUNCTION

(75) Inventor: Thomas John Harkins, Jr., Cherry Hill, NJ (US)

(73) Assignee: Health Knight, LLC, Cherry Hill, NJ (US)

( * ) Notice: Subject to any disclaimer, the term of this patent is extended or adjusted under 35 U.S.C. 154(b) by 1067 days.

(21) Appl. No.: 12/122,023

(22) Filed: May 16, 2008

(65) Prior Publication Data

US 2008/0287879 A1 Nov. 20, 2008

Related U.S. Application Data

(60) Provisional application No. 60/930,447, filed on May 16, 2007.

(51) Int. Cl.
*A61M 31/00* (2006.01)
*A61M 37/00* (2006.01)
*A61K 31/19* (2006.01)
*A61K 31/417* (2006.01)
*A61K 31/472* (2006.01)

(52) U.S. Cl.
CPC .............. *A61M 31/00* (2013.01); *A61K 31/19* (2013.01); *A61K 31/417* (2013.01); *A61K 31/472* (2013.01)

(58) Field of Classification Search
CPC ....... A61F 5/41; A61M 5/2448; A61M 5/284; A61M 5/31596; A61M 2210/167; A61M 2210/168; A61K 9/0034; B05C 17/00516
USPC .................. 604/514, 517, 276, 58–61, 82–92
See application file for complete search history.

(56) References Cited

U.S. PATENT DOCUMENTS

| | | | |
|---|---|---|---|
| 3,927,197 A | 12/1975 | Monkhouse | |
| 4,801,587 A | 1/1989 | Voss et al. | |
| 4,995,381 A | 2/1991 | Marmar et al. | |
| 5,242,391 A | 9/1993 | Place et al. | |
| 5,718,917 A * | 2/1998 | See ............................ | 424/450 |
| 5,741,523 A | 4/1998 | Teagarden et al. | |
| 5,820,587 A * | 10/1998 | Place ........................ | 604/500 |
| 5,942,545 A * | 8/1999 | Samour et al. ............. | 514/573 |

(Continued)

OTHER PUBLICATIONS

Muriel, Paul et al, "Stability of Prostaglandin E1 (PGE1) in Aqueous Solutions", EJHP, vol. 11, 2005, Issue 2, p. 31-36.*
Moriel et al, "Sodium Bicarbonate Allieviates Penile Pain Induced by Intracavernous Injections for Erectile Dysfunction", May 1993, Journal of Urology, vol. 149, 1299-1300.*

(Continued)

*Primary Examiner* — Andrew Gilbert

(57) ABSTRACT

A treatment for male erectile dysfunction comprising separately storing a lyophilized composition of vasoactive agents and a carrier gel, mixing said lyophilized composition of vasoactive agents and said carrier gel creating a homogeneous mixture and applying said homogeneous mixture to the meatus of the glans penis. A system for the treatment of male erectile dysfunction comprising a syringe coupling system for the storage, mixing and application of therapeutic compounds for the treatment of erectile dysfunction, said system further comprising a first syringe and a second syringe. The first and second syringes are filled with a lyophilized composition of vasoactive agents or a carrier gel. The system includes a locking device coupling said syringes to facilitate the transfer of said lyophilized composition of vasoactive agents and carrier gel between the syringes and a penile adapter for applying the therapeutic compounds for the treatment of erectile dysfunction to the meatus of the glans penis.

10 Claims, 5 Drawing Sheets

(56) References Cited

U.S. PATENT DOCUMENTS

| | | | |
|---|---|---|---|
| 6,071,272 A * | 6/2000 | Hoffman et al. | 604/500 |
| 6,224,573 B1 * | 5/2001 | Yeager et al. | 604/181 |
| 6,323,241 B1 * | 11/2001 | Yeager et al. | 514/573 |
| 6,414,027 B1 * | 7/2002 | Neal | 514/573 |
| 6,696,072 B1 * | 2/2004 | Podolski | 424/422 |
| 6,907,679 B2 * | 6/2005 | Yarborough et al. | 34/285 |
| 2003/0134903 A1 * | 7/2003 | Yeager et al. | 514/573 |
| 2003/0220292 A1 * | 11/2003 | Okada et al. | 514/54 |

OTHER PUBLICATIONS

Marmar, Harkins, Riordan; "Studies with Trimix Gel in Men Who Failed Phosphodiesterase Inhibitors"; The Journal of Urology; May 20, 2008; pp. 431; vol. 179, No. 4, Supplement; US.

Bennett, Guhring, Narus, Mulhall; "Satisfaction Profiles and Their Determinants in Men Using Intracavernosal Injection Therapy"; The Journal of Urology; May 20, 2008; pp. 431; vol. 179, No. 4, Supplement; US.

* cited by examiner

SYSTEM AND METHOD FOR TREATING ERECTILE DYSFUNCTION

This invention claims priority to provisional application 60/930,447, filed May 16, 2007.

FIELD OF THE INVENTION

The present invention generally relates to the storage, mixing and application of therapeutic compounds and specifically to a system and method for treating erectile dysfunction.

BACKGROUND OF THE INVENTION

As used herein, the term "erectile dysfunction" (ED) refers to certain disorders of the cavernous tissue of the penis and the associated facia which produce the inability to attain a sexually functional erection, priapism, the persistent and often painful erection of the penis, and Peyronie's syndrome, a condition characterized by fibrosis of the cavernous tissue and associated painful and distorted erection of the penis. Erectile dysfunction affects a substantial number of patients. ED can result from any of numerous physiological or psychological factors which cause the blood flow to and from the penis to remain in balance thereby preventing retention of sufficient blood to cause an erection. As used herein, the term "erectile dysfunction" is used in its broadest sense as the inability to attain a sexually functional erection when desired.

Millions of men suffer from ED and have sought an effective and pain free cure that can be sustained and presents no dangerous side effects. To that end, several therapies have become available, including penile implants, penile injection of vasoactive compounds, vacuum-constriction devices, PDE5 inhibiting pills and topical and intra-urethral vasoactive compounds. The penile implant was the first effective therapeutic method used for the treatment of ED (see Wilson S K and Delk J R II. Int J Imp Res. 4:S101-07, 2000). Over the years, implant designs have generally remained as either semi-rigid or inflatable. Additionally, due to the fact that they require surgery and have led to complications such as infection, rejection and mechanical failure, implants have usually remained as the method of last resort for most men. As a result, despite their effectiveness, only about 10-12,000 are placed each year in the United States. Therefore most men suffering from ED have searched for other alternatives to treat their condition.

The next effective therapy method used for the treatment of ED was penile injection with vasoactive drugs. Although this approach has been successful for many men, the drop out rate has proven to be high because most men are reluctant to self-inject the drugs and many have experienced pain and scarring as a result of the injections. Furthermore, the long-term stability of the compounds used for this method requires that they be refrigerated or maintained under special conditions for transport by the patients. Several patents, including U.S. Pat. Nos. 3,927,197 and 5,741,523, have been issued for the development of chemical formulations utilizing vasoactive compounds to reduce pain and improve stability.

Another method for treating ED, which has proven effective for many users, is vacuum erection devices with constriction rings. Some current systems, including U.S. Pat. No. 4,995,381, have achieved FDA approval because they have been engineered with safety features such as pressure governors, quick release valves and safe constriction rings. Like the use of vasoactive gels, these systems can also be used in combination with other therapies. However, the use of vacuum devices with constriction rings is unattractive to many prospective users because the mechanical apparatus can be intimidating and the method is not conducive to spontaneous use.

The availability of phosphodiesterase type 5 (PDE5) inhibitors has made a great impact on the treatment of ED. These drugs, available in tablet form, have been taken by millions of men and they have also been used for men with comorbidities. However, these tablets present some major negative drawbacks. For instance, PDE5 inhibitors cannot be used for men using nitroglycerine products or that have a history of retinal problems. In addition, PDE5 inhibitors have also been shown to cause headaches and nasal congestion. For these reasons, there are many dropouts associated with these medications; leading to a search for alternative treatments for ED (see Rupesh R et al. J Androl. 26:757-60, 2005).

Recently, the use of topical and intra-urethral products has received attention because they are readily transportable, minimally invasive and have the potential for use with combination therapy. Several patents have been granted to inventors who described topical products and delivery systems related to the treatment of ED. For example, U.S. Pat. No. 4,801,587 describes a gel containing a combination of vasodilators. The product is placed topically on the penis, and then into the urethra using a catheter. The urethra was chosen for application because, unlike the penile skin, the urethral mucosa is not keratinized and contains specific receptor sites and many other drug products have been placed there for absorption (see Holstein A F et al. Cell Tiss. Res. 264:23-32, 1991, Pudney J and Anderson D J. Amer. J. Path. 147:155-165, 1995 and DeBenedictis T J et al. J Urol. 118:767-769, 1977). U.S. Pat. No. 5,242,391 discloses an invention of a coated pellet containing Prostaglandin Subgroup 1 (PGE1) and a dispenser for insertion into the urethra. This product has been sold and used in clinical practice under the trade name MUSE. Although this product has had positive responses among a variety of ED patients, many reports also suggest that users have experienced pain from insertion of the dispenser and a throbbing pain as a direct result of the PGE1 product in 35-60% of the cases (see Linet et al. NEJM 334: 873, 1996).

For this reason, alternative solutions of ED treatment using pre-mixed PGE1 based compositions have been sought. For example, U.S. Pat. No. 6,323,241 discloses an invention of a PGE1 gel with several chemical ingredients including penetration enhancers and a buffer system to maintain a final pH in the range of 3-7.4. While this product was reported to have a 73.1% satisfaction rate, 14.6% of the patients complained of pain (see Zhao D et al. Zhonghua Nan Ke Xue 9:48-50, 2003).

It has been suggested that there is a relation to the pain caused by topical methods and the PH level of the pre-mixed product. Some studies have shown that higher pH levels have reduced the amount of pain associated with the use of PGE1 (see Moriel E Z and Rajfer J. J Urol. 149 1299-300, 1993). However, it is difficult to maintain the pH level of pre-mixed PGE1 based products because the ingredients may precipitate upon standing at a higher pH. Further disadvantages of pre-mixed PGE1 compositions include a short shelf life that requires products to be used immediately to achieve the desired results and the requirement for special additives that adds to the cost and complexity of the system.

All of the therapies mentioned above have been used for the definitive treatment of ED, but each has been shown to have limitations. As a result, many men are reluctant to try some of these methods and those who have used one or more of these methods have discontinued use because of side effects or a failure to consistently achieve desired results. Therefore, there is an on-going need for improved methods of treatment for men with ED. In accordance, the present system represents a simplified approach to the storage, mixing and intra meatal delivery of a vasoactive gel.

SUMMARY OF THE INVENTION

Accordingly, it is an object of the present invention to provide a system and method for the treatment of erectile dysfunction (ED). The method of treating erectile dysfunction comprises the steps of separately storing a lyophilized composition of vasoactive agents and a carrier gel, mixing the lyophilized composition and the carrier gel to create a homogeneous mixture and applying the homogeneous mixture to the glans penis.

Another object of the present invention is that the resultant homogeneous mixture of vasoactive agents and a carrier gel has a PH level above 9 to reduce the pain associated with the application of vasoactive agents.

Another object of the present invention is to lyophilize the vasoactive agents. This allows the vasoactive agents to be stored for a longer period of time and then to be mixed with the carrier gel immediately before application to maximize results.

Another object of the present invention is to allow the lyophilized composition of vasoactive agents and a carrier gel to be stored separately from each other. This allows the compositions to have a longer shelf life so the treatment will be available to patients when needed and the resulting mixture can be maintained at the desired pH level.

It is yet another object of the current invention to provide a system to store and mix a lyophilized composition of vasoactive agents and a carrier gel.

Another object of the present invention is that the mixing system comprises a first and second syringe, each syringe storing either the lyophilized composition of vasoactive agents or the carrier gel. The system also includes a locking device which allows the syringes to be coupled together. The coupled syringes allow for the transfer of lyophilized composition of vasoactive agents and the carrier gel between the two syringes to create a homogeneous mixture. The system also discloses a penile adapter capable of applying the homogeneous mixture to the glans penis.

Another object of the present invention is to provide a penile adapter capable of creating a seal with the meatus of the glans penis so therapeutic compounds can be applied to the meatus of the glans penis without any leakage.

Another object of the present invention is that the penile adapter is configured to fit over a device which stores and discharges medicinal compounds, such as a syringe, and allows users to easily and safely apply the therapeutic agents themselves.

Another object of the present invention is to provide a method of storing, mixing and applying a therapeutic compound for the treatment of erectile dysfunction comprising the steps of storing a lyophilized composition of vasoactive agents in a first syringe, storing a carrier gel in a second syringe and mixing said lyophilized composition of vasoactive agents and said carrier gel using a device adapted for coupling said syringes together, said device allowing the transfer of said lyophilized composition of vasoactive agents and said carrier gel between said syringes, the repeated transfer creating a homogeneous mixture for erectile dysfunction treatment. The method also comprises the steps of transferring said homogeneous mixture for erectile dysfunction treatment into said first syringe, fitting a penile adapter to said first syringe and discharging said homogeneous mixture for erectile dysfunction treatment into the glans penis.

BRIEF DESCRIPTION OF THE FIGURES

The object and the advantages of various embodiments of the invention will become apparent from the following description when read in conjunction with the accompanying drawings wherein.

FIG. 5b is a cross-sectional view of the penile adapter shown in FIG. 5a.

DETAILED DESCRIPTION OF THE EMBODIMENTS

Figure 1:
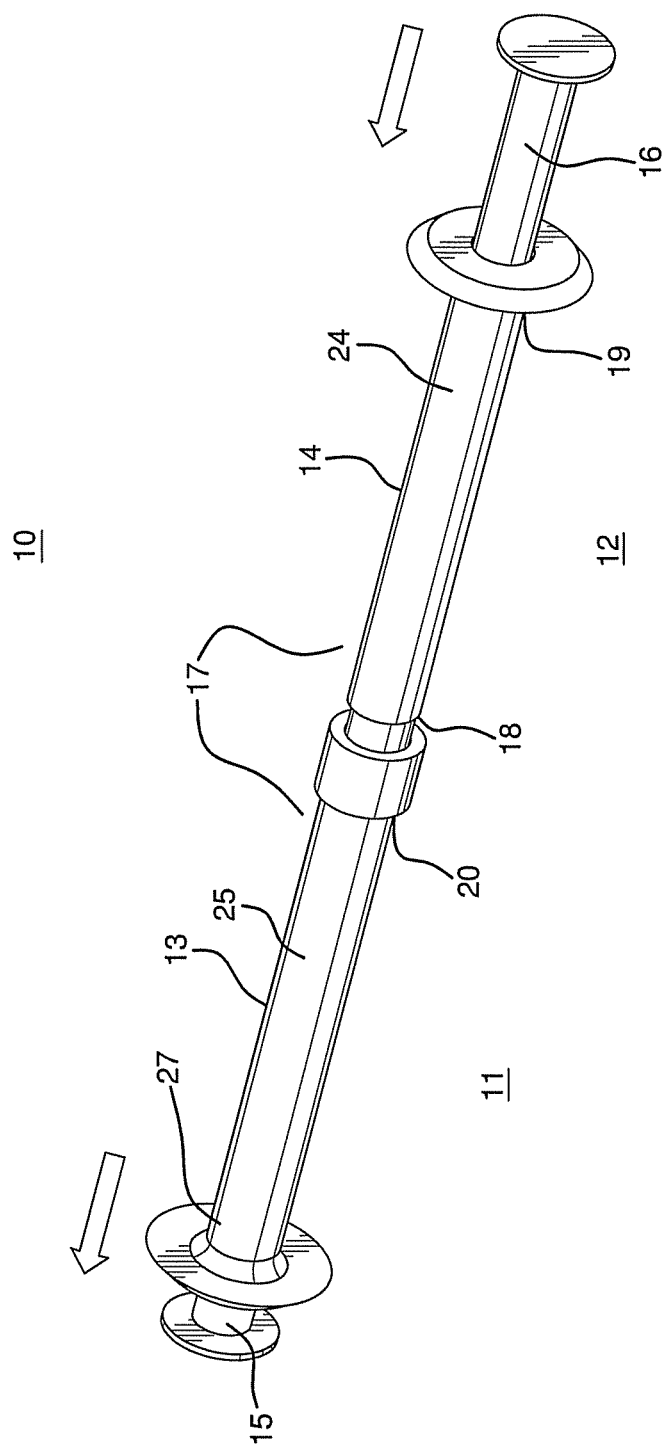
FIG. 1 is a perspective view of a syringe coupling system, according to an embodiment of the present invention.

The present invention teaches a system and method to treat erectile dysfunction (ED). In its broadest aspect, the invention contemplates a method of intra meatal delivery of therapeutic agents to the mucosa of navicular fossa. The erectile dysfunctions may be so treated with therapeutic agents comprising one or more drugs capable of producing a vasodilatory or other erection inducing effect.

The term "meatus" refers to a natural body opening or canal.

The term "glans penis" refers to the sensitive tip or head of the penis.

The term "mucosa" refers to linings of body cavities which are involved in absorption and secretion.

The term "navicular fossa" refers to the cavernous portion of the urethra.

The term "lyophilize" refers to a dehydration process typically used to preserve a perishable material or make the material more convenient for transport.

The term "vasodilator" refers to a drug or chemical that relaxes the smooth muscle in blood vessels, which causes them to dilate.

The term "vasoactive" refers to a drug or chemical with vasodilatory properties.

The therapeutic agents used in the present invention comprise one or more vasodilators and a vasoactive prostaglandin. Suitable vasodilators include alpha-adrenergic blockers (e.g., phentolamine or any pharmaceutically acceptable salt of phentolamine) and papaverine or any pharmaceutically acceptable salt of papaverine. Suitable vasodilators include atropine, niacin, prazosin, doxazosin, terazosin and minoxidil and mixtures thereof. Accordingly, it is appreciated that those skilled in the art may utilize any suitable vasodilatory agent or any pharmaceutically acceptable salts of these vasodilators. Suitable vasoactive prostaglandins include prostaglandin E1, alprostadil, prostaglandin E2, synthetic prostaglandins, misoprostol, enprostil, and analogs thereof.

Accordingly, it is appreciated that those skilled in the art may utilize any suitable vasoactive prostaglandin.

The present invention discloses the novel approach of using a lyophilized composition of one or more vasodilators and a vasoactive prostaglandin for the treatment of ED. Utilizing a lyophilized composition presents the advantage of an increased shelf life so that the therapeutic agents can be stored for a longer period until the user is ready to administer a dosage. In a preferred embodiment, the lyophilized composition of vasoactive agents comprises papaverine, phentolamine and alprostadil. In one embodiment, the lyophilized composition of vasoactive agents comprises 1000 mcg alprostadil, 300 mcg papaverine and 100 mcg phentolamine. In another embodiment, the lyophilized composition of vasoactive agents comprises 500 mcg alprostadil, 300 mcg papaverine and 100 mcg phentolamine. In yet another embodiment, the lyophilized composition of vasoactive agents comprises 250 mcg alprostadil, 300 mcg papaverine and 100 mcg phentolamine. Accordingly, it is appreciated that those skilled in the art may use a lyophilized composition containing any pharmaceutically effective amount of alprostadil, papaverine and phentolamine.

The use of a lyophilized composition also allows the vasoactive agents to be stored until the time of application. At the time of application, the lyophilized composition of vasoactive agents is combined with a pharmaceutically suitable amount of a carrier gel to create a homogenous mixture to be applied to the glans penis. Suitable carrier gels include high weight cellulose gels such as methylcellulose, polyethylene glycol, propylene glycol, glycerin and hydroxyethyl cellulose. Accordingly, it is appreciated that those skilled in the art may utilize a pharmaceutically effective amount of any suitable high weight polymer gel.

A common problem experienced with pre-mixed gels of the prior art that high pH levels could not be maintained. By avoiding the use of pre-mixed gels, the present invention allows the pH level of the final mixture of vasoactive agents and carrier gel to be maintained. As vasoactive agents have been shown to cause less pain and discomfort at higher pH levels, in a preferred embodiment, the pH level for the homogenous mixture of vasoactive agents and carrier gel is greater than 9.

In a preferred embodiment, pain-relieving additives are also added to the carrier gel to reduce the pain associated with the application of vasoactive agents to the urethra of the penis. Suitable additives include lactose, molar potassium phosphate, sodium bicarbonate and mixtures thereof. Accordingly, it is appreciated that those skilled in the art may also utilize any suitable pain relieving additives to be combined with the carrier gel.

FIG. 1 discloses a system for coupling two syringes that can be used to mix a lyophilized composition of vasoactive agents and carrier gel, according to an embodiment of the present invention. The syringe coupling system 10 includes a first syringe 11 and a second syringe 12, which are designed to be coupled together so as to pass the lyophilized vasoactive agents and carrier gel therebetween. Further disclosure with regard to the configuration and coupling of the syringes and mixing of components between the two syringes is disclosed in U.S. Pat. No. 6,234,196 issued on May 22, 2001 and U.S. Pat. No. 6,610,034 issued on Aug. 26, 2003, which are incorporated herein by specific reference.

Figure 2:
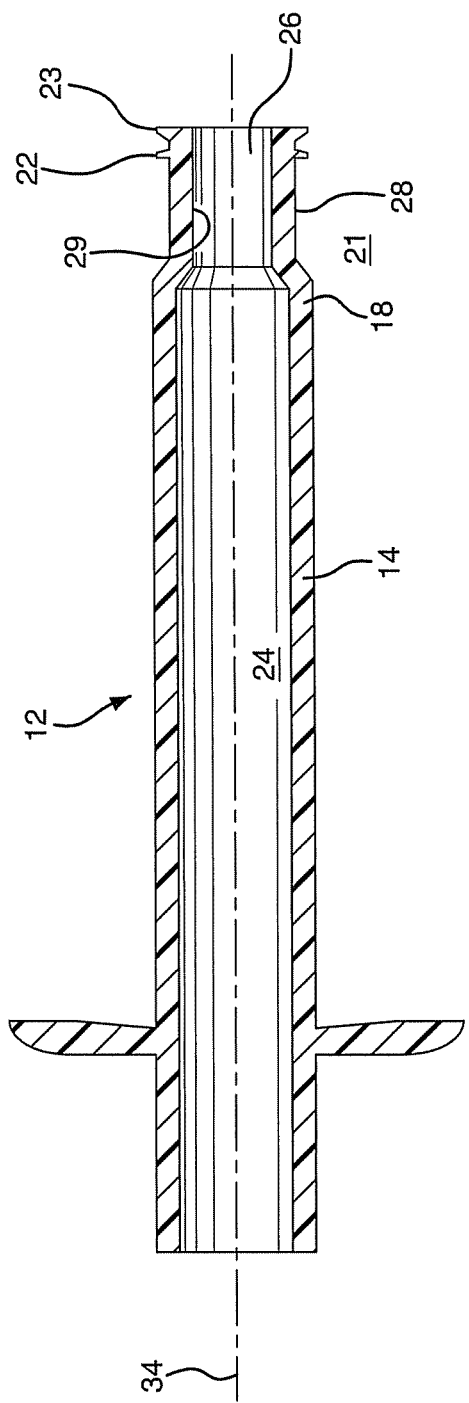
FIG. 2 is an enlarged side view of the second syringe shown in FIG. 1.

As shown in FIGS. 1 and 2, second syringe 12 includes a barrel 14 having a first end 18 and an opposing second end 19. Projecting from the first end 18 is a tubular tip 21. Slideably disposed within the second end 19 of barrel 14 is a plunger 16. Barrel 14 also bounds cavity 24. Cavity 24 is configured to slidably receive plunger 16 and to hold either the lyophilized vasoactive agents or carrier gel for mixing and/or dispensing.

Tubular tip 21 of second syringe 14 is shown having an exterior surface 28 and an opposing interior surface 29. Interior surface 29 bounds a channel 26 in fluid communication with cavity 24. A central longitudinal axis 34 extends through cavity 24 and chamber 26. In the embodiment depicted, the tubular tip 21 has a smaller outer diameter than the barrel 14. In alternative embodiments, however, the tubular tip 21 may have the same or other varied diameter relative to barrel 14. In such embodiments, the tubular tip 21 merely defines one end of barrel 14.

Still referring to FIGS. 1 and 2, outwardly projecting from the exterior of the tubular tip 21 is a pair of spaced apart first threads 22 and 23. In one embodiment, first threads 22 and 23 comprise a pair of right hand threads. In the embodiment depicted, each of first threads 22 and 23 only partially encircle tip 21. In alternative embodiments, one or both of first threads 22 and 23 may completely encircle tip 21 one or more times.

Figure 3:
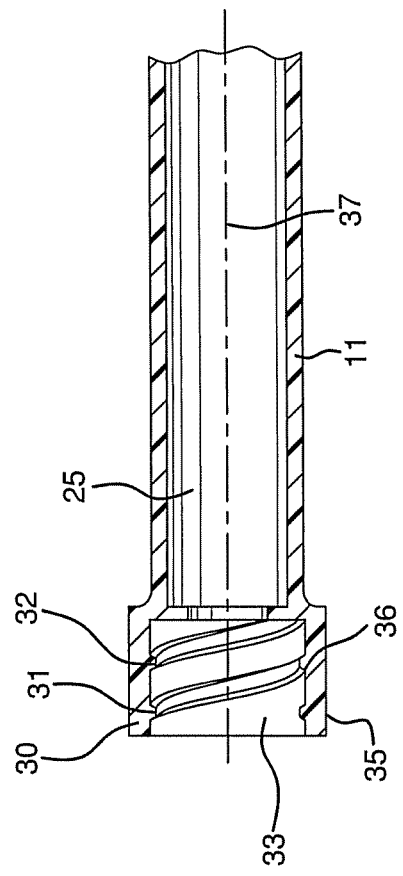
FIG. 3 is an enlarged side view of the first syringe shown in FIG. 1.

Referring now to FIGS. 1 and 3, the first syringe 11 includes a barrel 13 having a first end 20 and an opposing second end 27. Slidably disposed within the second end 27 of barrel 13 is a plunger 15. Barrel 13 bounds a cavity 25 that is configured to slidably receive plunger 15 and to hold either the lyophilized vasoactive agents or carrier gel for mixing and/or dispensing. A tubular collar 30 having an exterior surface 35 and an opposing interior surface 36 projects from the first end 20 of barrel 13. Inwardly projecting from interior surface 36 of collar 30 is a pair of engagement threads 31 and 32. Interior surface 36 bounds a channel 38 that is in fluid communication with cavity 25. A central longitudinal axis 37 extends through cavity 25 and chamber 38.

Figure 4:
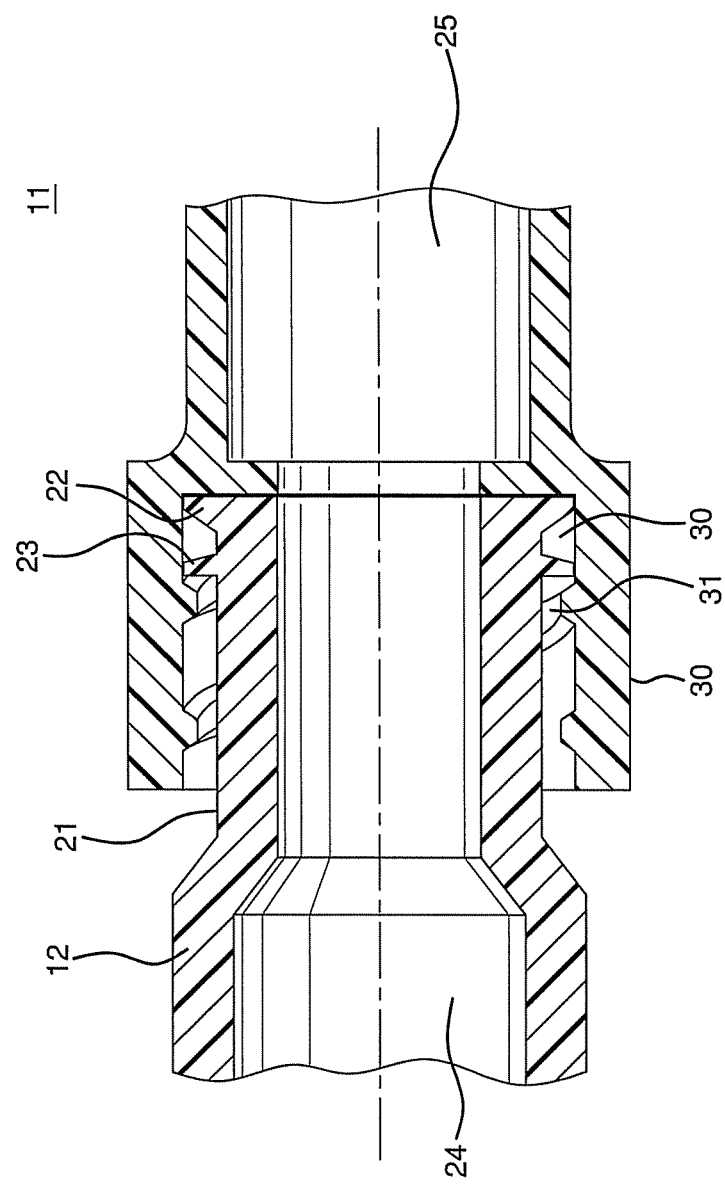
FIG. 4 is an exploded view showing the syringe coupling system shown in FIG. 1.

As depicted in FIG. 4, the first syringe 11 and second syringe 12 are locked together such that tubular tip 21 can be selectively received within channel 25 and secured therein by threaded engagement between first threads 22, 23 and engagement threads 31 and 32. In this coupled engagement, cavities 24 and 25 are in fluid communication. By selectively advancing one of plungers 15 or 16, the component within the syringe of the advancing plunger is passed into the cavity of the opposing syringe. Furthermore, by selectively advancing and retracting each of plungers 15 and 16, the lyophilized vasoactive agents and carrier gel within each of syringes 11 and 12 can be passed back and forth between the two syringes, thereby mixing the two components and creating a homogeneous mixture for erectile dysfunction treatment.

Figure 5A:
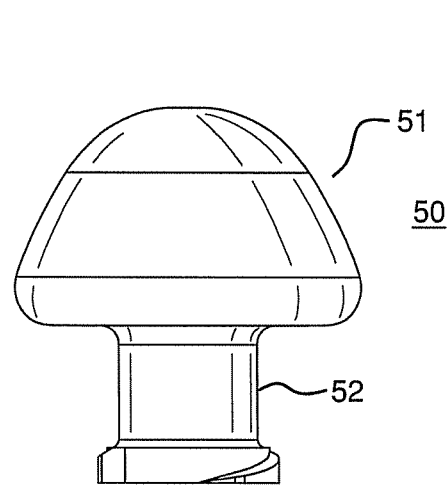
FIG. 5a is a perspective view of a penile adapter, according to an embodiment of the present invention.
Figure 5B:
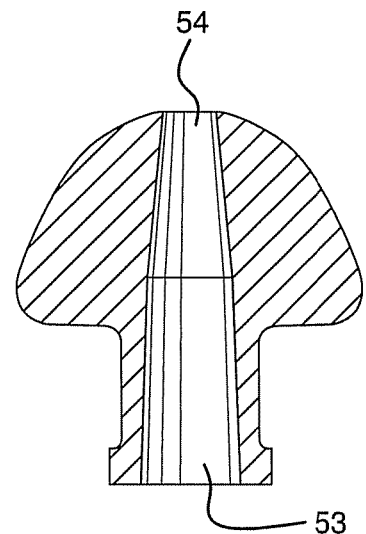
Figure 6:
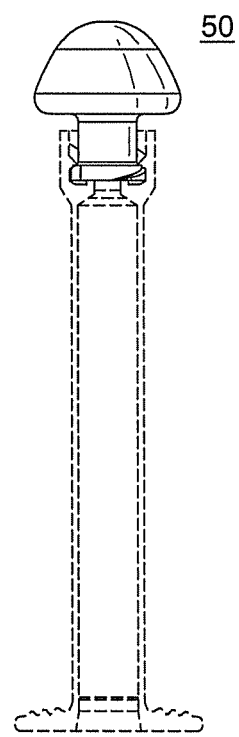
FIG. 6 is a perspective view of the penile adapter of FIG. 5a fitted to a syringe.

Referring now to FIGS. 5a, 5b and 6, a penile adapter, according to a preferred embodiment of the present invention, will be described. As best seen in FIG. 5a, the penile adapter is formed from a top portion 51 and bottom portion 52. The top portion 51 has a substantially spheroidal dome shape and is designed to create a seal with the meatus of the glans penis. The slope of the top portion 51 allows it to create a substantially liquid tight seal with any size meatus. When the penile adapter 50 is placed on the glans penis, the top portion 51 fits within the meatus to prevent the therapeutic compounds being applied to the mucosa of the urethra from being lost or leaking onto the penis. In addition, the top portion 51 is designed such that no portion of a device being used to discharge therapeutic compounds penetrates past the meatal opening of the glans penis. This prevents any unnecessary discomfort or pain during the application of therapeutic compounds. The placement of the top portion 51 of the penile adapter also acts to massage the meatus of the glans penis, which has shown to improve absorption and the effectiveness of the therapeutic agents. The bottom portion 52 of the penile adapter 50 has a substantially cylindrical shape and extends perpendicularly from the top portion 51 of the penile adapter 50. As shown in FIG. 5b, the penile adapter 50 has a rearward open channel 53 in the bottom portion 52 and a forward open channel 54 in the top portion 51. The rearward open channel and the forward open channel are in fluid communication to facilitate the flow of therapeutic compounds. The bottom portion 52 of the penile adapter 50 can be removeably attached to a device, such as a syringe, that discharges medicinal compounds. The penile adapter can be made from a polyethylene-based material in order to not cause irritation to human tissue. FIG. 6 depicts a preferred embodiment wherein the penile adapter 50 is fit to a syringe.

Figure 7:
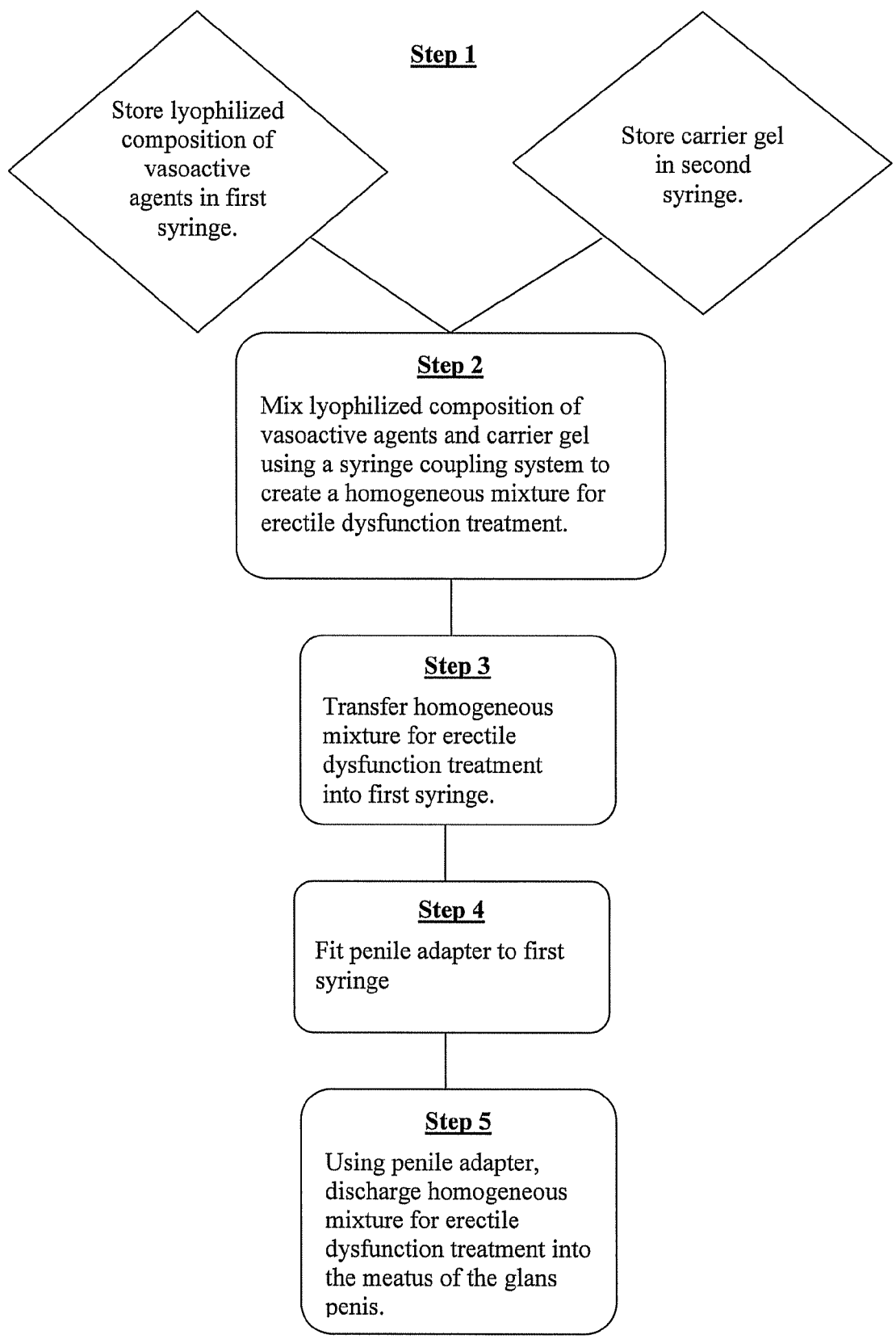
FIG. 7 is a flow diagram showing the steps of storing, mixing and applying therapeutic compounds for erectile dysfunction treatment.

Referring now to FIG. 7, the method of storing, mixing and applying therapeutic agents for the treatment of erectile dysfunction will be described. In step 1, a pharmaceutically suitable amount of a lyophilized composition of vasoactive agents and carrier gel are stored separately in two syringes. By separately storing the ingredients, the shelf life of the vasoactive agents is lengthened. There is also no need for additives to maintain the homogeneous mixture or desired pH level.

In step 2, the lyophilized composition of vasoactive agents and carrier gel are vigorously mixed using a syringe coupling system. Using a syringe coupling system, the two syringes are linked to allow transfer of the vasoactive agents and carrier gel therebetween. After the syringes are securely locked to each other, the plungers of each syringe are alternately depressed and retracted so that the product within one syringe will be transferred to the other syringe. This process is repeated rapidly about 20 to 30 times to insure that the vasoactive agents and gel become a homogeneous mixture. The locking system will permit a series of vigorous and repeated transfers leading to complete combination of the products without any internal precipitate formation. The final homogeneous mixture creates a gel in which the products are dissolved completely and are available at full strength for absorption through the mucosa of the urethra. The final mixture will have a pH above 9 for maximum effectives and to reduce the pain during application. Although the higher pH has produced precipitation in other situations, the vigorous mixing achieved with the present invention produces a homogeneous gel that is able to maintain at the desired pH level. At step 3, the homogeneous mixture is transferred into the syringe which is configured to accept the bottom portion of the penile adapter. The other syringe can then be disconnected and discarded.

At step 4, the penile adapter is securely fit to the syringe containing the homogenous mixture. Finally, at step 5, the penile adapter is placed over the meatus of the glans penis. The shape of the penile adapter creates a seal with the meatus so that the homogeneous mixture can be applied to the urethra without any leakage. The shape of the penile adapter also prevents any penetration beyond the meatal opening to prevent pain and discomfort during application. The homogenous mixture can then be discharged from the syringe, through the penile adapter and directly into the navicular fossa. The homogeneous mixture is then rapidly absorbed through the mucosa of navicular fossa within minutes.

EXAMPLE 1

The system and method for treating erectile dysfunction described above was evaluated for administration at the urethral meatus. In this test, Erection Hardness Scores (EHS) and penile rigidity studies were recorded after the mixture of lyophilized vasoactive agents and a carrier gel was used on forty-two men with mixed morbidities who failed with PDE5 oral agents. Sixteen of the men were on antihypertensive meds, twelve had type II diabetes, eight had high cholesterol and six were post radical prostatectomy. Ten of the men tested also had comorbidies. Prior to administration of the mixture of lyophilized vasoactive agents and a carrier gel, an EHS for each man was recorded after the use of an oral agent. The lyophilized vasoactive agents and 0.3 ml of carrier gel were maintained in separate interlocking syringes at room temperature until the time of use. The final preparation was completed by vigorous mixing between the interlocking syringes as described in the specification above. The mixture was inserted painlessly into the urethral meatus and the patient massaged the outer glans for two minutes to promote absorption. There was no other form of stimulation. After application, an EHS was recorded for each patient. In addition, nine had measurement of buckling pressures and seven had rigiscans. For all forty-two patients (mean age 55.2 yrs), the EHS was recorded as 1 after use of the oral agents (penis was larger but not hard), but twenty-two of these patients actually had no increase in size. After the application of the mixture of vasoactive agents and gel, the mean EHS was 2.2; with eleven patients having an EHS of 3 (26.1%) and 6 with an EHS of 4 (16.6%). Thus, 40.4% of the study group had erections that were sufficient for penetration. In those with an ESH of 4, the buckling pressure was >90 mm Hg. The rigiscans provided real time information about the gel response and documented some tumescence in all cases. The result of the tests showed that the application of a lyophilized composition of vasoactive agents and a carrier gel mixed immediately before application effectively treated erectile dysfunction and may have several advantages over oral agents and intracavernous injections.

Finally, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for the treatment of male erectile dysfunction comprising the steps of:
   storing a lyophilized composition of vasoactive agents separately from a carrier gel in a gel state;
   mixing said lyophilized composition of vasoactive agents and said carrier gel at or immediately before a time of application to create a homogeneous mixture for erectile dysfunction treatment, said homogeneous mixture having a gel state;
   placing an insertion apparatus on a glans penis, said glans penis having a meatus, said meatus having a meatal opening, such that no part of a top portion of the insertion apparatus extends past the meatal opening; and
   using the insertion apparatus to insert said homogeneous mixture into the meatus
   wherein the top portion has a spherical dome shape and a slope configured to create a liquid tight seal between the insertion apparatus and the meatus without regard to a size of the meatus.

2. The method claim 1, wherein said lyophilized composition of vasoactive agents comprises one or more vasodilators and a vasoactive prostaglandin.

3. The method of claim 2, wherein said vasoactive prostaglandin is selected from the group consisting of prostaglandin E1, alprostadil, prostaglandin E2, synthetic prostaglandins, misoprostol, enprostil, and analogs thereof.

4. The method of claim 2, wherein said one or more vasodilators comprises an alpha-adrenergic blocker and a phosphodiesterase inhibitor.

5. The method of claim 2, wherein said one or more vasodilators are selected from the group consisting of papaverine, phentolamine, atropine, niacin, prazosin, doxazosin, terazosin, minoxidil and mixtures thereof.

6. The method of claim 2, wherein said lyophilized composition of vasoactive agents comprises alprostadil, papaverine and phentolamine.

7. The method of claim 1, wherein said carrier gel is a high-weight cellulose based gel.

8. The method of claim 1, wherein said carrier gel further comprises at least one pain-reducing additive.

9. The method of claim 1, wherein said homogeneous mixture for erectile dysfunction treatment has a pH level of at least 9.

10. A method for delivering medication comprising the steps of:
- storing a lyophilized composition of pharmaceutical ingredients separately from a carrier gel in a gel state;
- mixing said lyophilized composition of pharmaceutical ingredients and said carrier gel at or immediately before a time of application to create a homogeneous mixture, said homogeneous mixture having a gel state;
- placing an insertion apparatus on meatal opening of a meatus of a human urethra, such that no part of a top portion of the insertion apparatus extends past the meatal opening; and
- using the insertion apparatus to insert said homogeneous mixture into the meatus;
- wherein the top portion has a spherical dome shape and a slope configured to create a liquid tight seal between the insertion apparatus and the meatus without regard to a size of the meatus.

* * * * *